(12) United States Patent
Biedermann et al.

(10) Patent No.: US 9,326,805 B2
(45) Date of Patent: May 3, 2016

(54) DYNAMIC BONE ANCHOR

(71) Applicant: Biedermann Technologies GmbH & Co. KG, Donaueschingen (DE)

(72) Inventors: Lutz Biedermann, VS-Villingen (DE); Timo Biedermann, Trossingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 132 days.

(21) Appl. No.: 14/139,678

(22) Filed: Dec. 23, 2013

(65) Prior Publication Data

US 2014/0188180 A1 Jul. 3, 2014

Related U.S. Application Data

(60) Provisional application No. 61/746,367, filed on Dec. 27, 2012.

(30) Foreign Application Priority Data

Dec. 27, 2012 (EP) ..................................... 12199487

(51) Int. Cl.
*A61B 17/04* (2006.01)
*A61B 17/84* (2006.01)
*A61F 2/08* (2006.01)
*A61B 17/86* (2006.01)
*A61B 17/80* (2006.01)
*A61B 17/00* (2006.01)
*A61B 17/70* (2006.01)

(52) U.S. Cl.
CPC ......... *A61B 17/8625* (2013.01); *A61B 17/8685* (2013.01); *A61B 17/7037* (2013.01); *A61B 17/80* (2013.01); *A61B 17/863* (2013.01); *A61B 17/866* (2013.01); *A61B 17/8615* (2013.01); *A61B 2017/00867* (2013.01)

(58) Field of Classification Search
None
See application file for complete search history.

(56) References Cited

U.S. PATENT DOCUMENTS 5,209,753 A 5/1993 Biedermann et al.
(Continued)

FOREIGN PATENT DOCUMENTS

JP 06-125918 5/1994
WO WO 95/15726 6/1995

OTHER PUBLICATIONS

Extended European Search Report for Application No. 12199487.5, European Search Report dated Jun. 11, 2013 and mailed Jun. 20, 2013 (14 pgs.).

(Continued)

*Primary Examiner* — Sameh Boles
(74) *Attorney, Agent, or Firm* — Lewis Roca Rothgerber Christie LLP

(57) ABSTRACT

A dynamic bone anchor includes a longitudinal core member having a first end and a second end, and a longitudinal axis extending through the first end and the second end. The dynamic bone anchor further includes a plurality of tubular segments configured to be positioned around the core member, each of the tubular segments having a bone engagement structure on an outer surface thereof. In a first assembled configuration between the core member and the tubular segments, each of the tubular segments is individually movable on the core member along the longitudinal axis independent of the core member, itself, and the other tubular segments.

21 Claims, 11 Drawing Sheets

(56) References Cited

U.S. PATENT DOCUMENTS

| | | | |
|---|---|---|---|
| 2007/0038219 A1* | 2/2007 | Matthis | A61B 17/864 623/17.11 |
| 2009/0157123 A1 | 6/2009 | Appenzeller et al. | |
| 2009/0248089 A1 | 10/2009 | Jacofsky et al. | |
| 2010/0082071 A1 | 4/2010 | Moumene | |

OTHER PUBLICATIONS

Partial European Search Report for Application No. 12199487.5, European Search Report dated Apr. 11, 2013 and mailed Apr. 22, 2013 (6 pgs.).

* cited by examiner

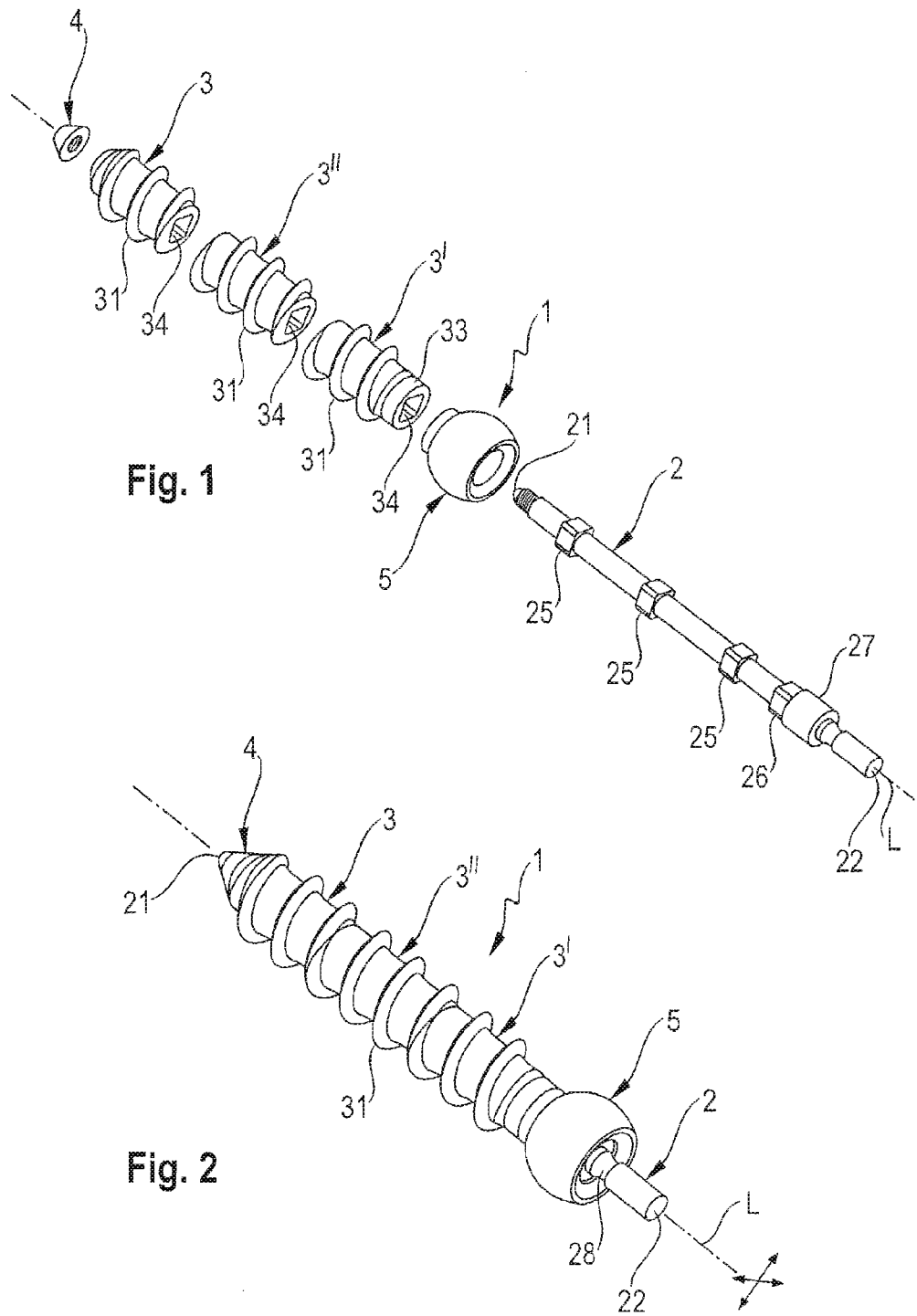

Fig. 3
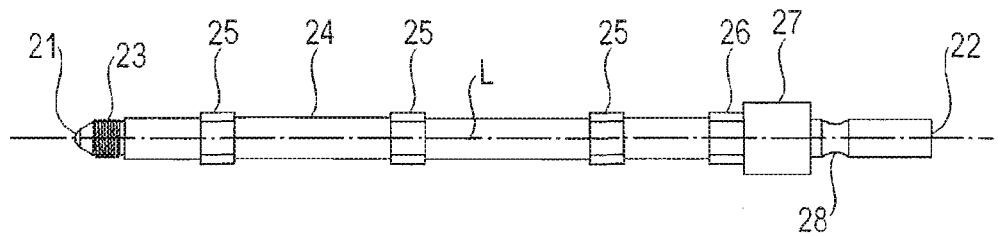
Fig. 4
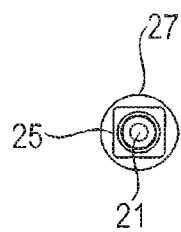
Fig. 5
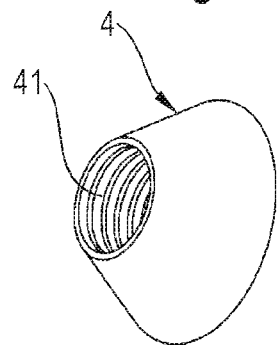
Fig. 6
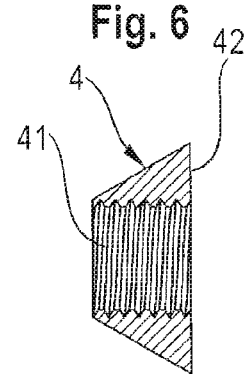
Fig. 7
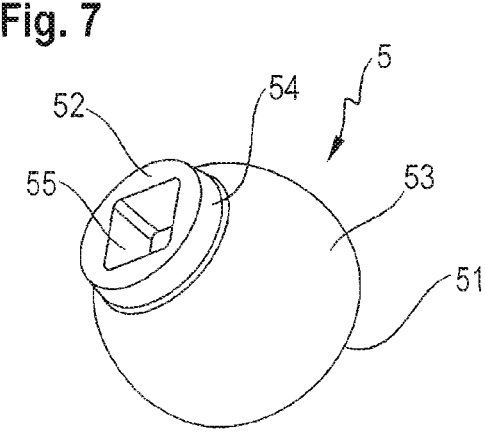
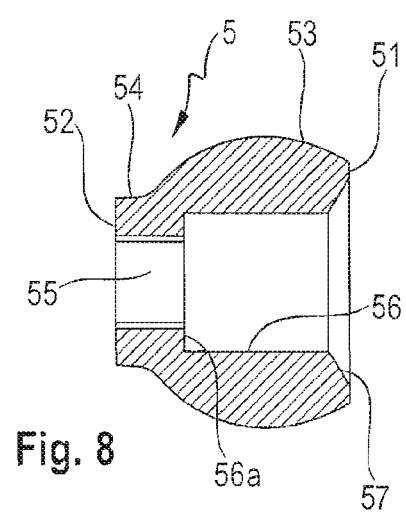
Fig. 8

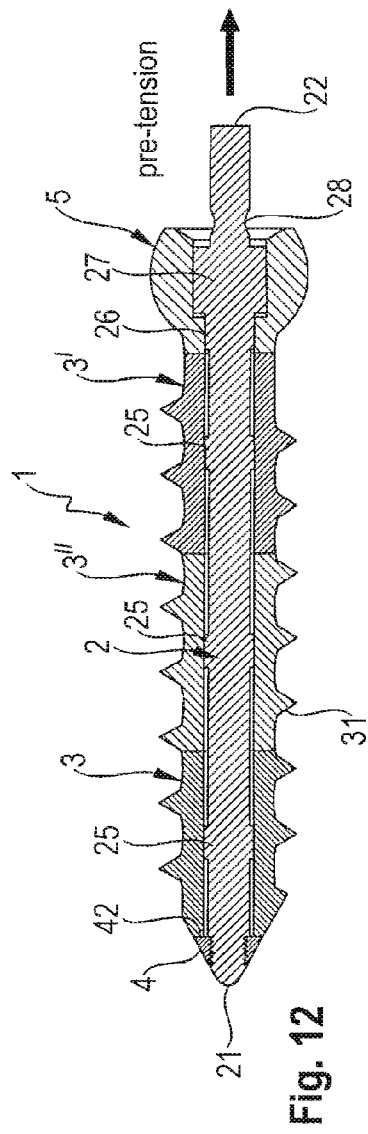
Fig. 12
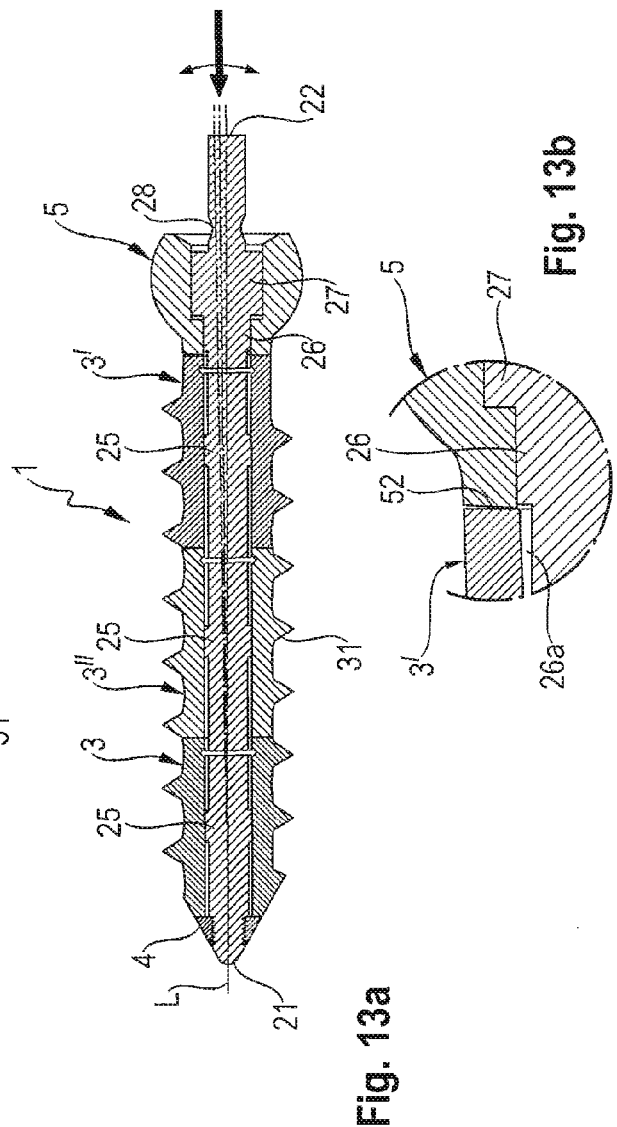
Fig. 13a
Fig. 13b

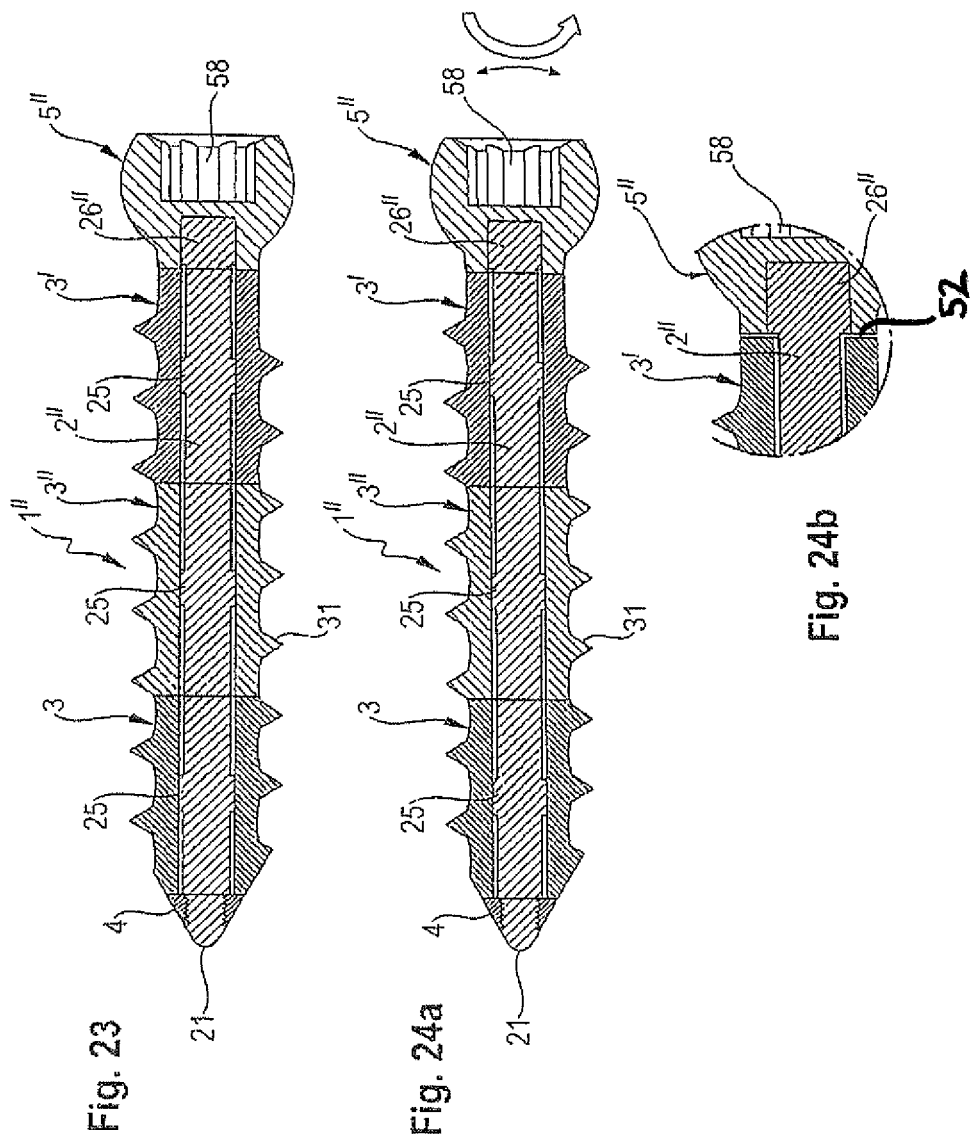

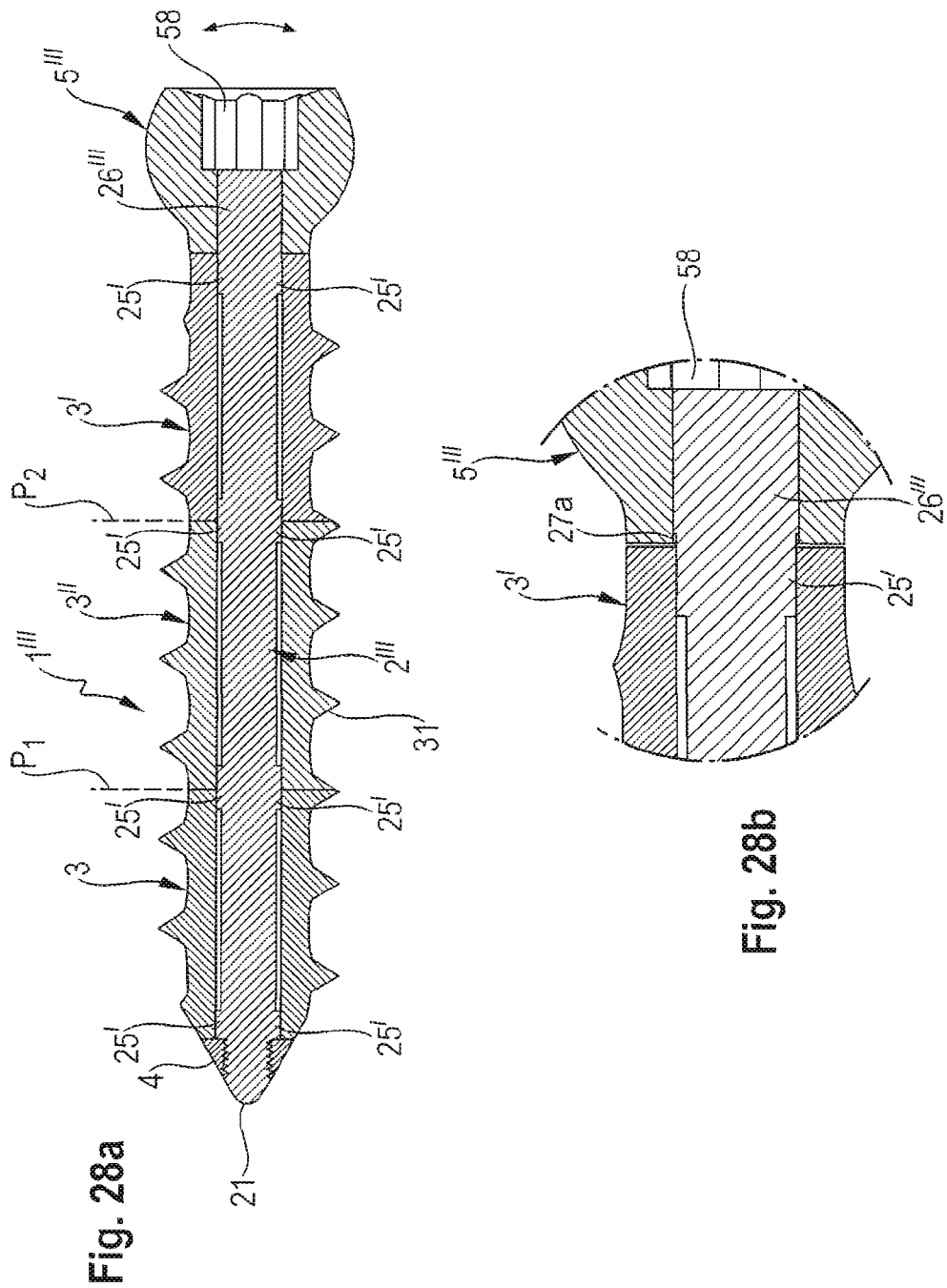

DYNAMIC BONE ANCHOR

CROSS-REFERENCE TO RELATED APPLICATIONS

This application claims priority to and the benefit of U.S. Provisional Patent Application No. 61/746,367, filed on Dec. 27, 2012, in the U.S. Patent and Trademark Office, the entire contents of which is incorporated herein by reference; and claims priority from European Patent Application EP 12 199 487.5, filed Dec. 27, 2012, the entire contents of which is incorporated herein by reference.

BACKGROUND

1. Field

The invention relates to a dynamic bone anchor. The dynamic bone anchor comprises a longitudinal core member and a plurality of tubular segments provided on the core member. In a first configuration, there is a distance between the tubular segments in the longitudinal direction and the tubular segments are movable relative to one another. When the bone anchor is in the first configuration, the core member can perform small movements transverse to a longitudinal axis. In an optional second configuration, the tubular segments abut against each other and cannot move. The dynamic bone anchor can be used in any kind of bone fixation or stabilization device, such as pedicle screws or bone plates, for the purpose of allowing a limited motion of components of the device.

2. Description of the Related Art

A dynamic bone fixation element is known from US 2009/0157123 AI. The dynamic bone fixation element includes a bone engaging component and a load carrier engaging component. The bone engaging component includes a plurality of threads for engaging a patient's bone, and a lumen. The load carrier has a shaft portion that at least partially extends into the lumen. A distal end of the shaft portion is coupled to the lumen, and at least a portion of an outer surface of the shaft portion is spaced away from at least a portion of an inner surface of the lumen via a gap, such that the head portion can move with respect to the bone engaging component.

SUMMARY

It is an object of the invention to provide a dynamic bone anchor that allows for limited motion of a head of the bone anchor after anchoring the bone anchor into a bone or a vertebra.

With the dynamic bone anchor, bone parts or vertebrae to be fixed or stabilized are able to carry out a controlled limited motion relative to each other. In particular, the head of the bone anchor can perform a small rotational and/or translational motion with respect to a central axis of the bone anchor.

In the assembled state, the bone anchor can assume a first configuration in which the head is movable, and, optionally, a second configuration in which the whole bone anchor is a rigid device. The configuration of the dynamic bone anchor may be changed between the first configuration and the second configuration. In some embodiments, the second configuration may be used during insertion of the bone anchor into a bone part or vertebra. Because the bone anchor may be rigid during insertion, an easy insertion in a known manner is possible. The bone anchor may be in the first configuration after implantation of the bone anchor.

A bone engagement structure of the dynamic bone anchor may be a bone thread or another engagement structure such as barbs or the like. If the bone engagement structure is a bone thread, the thread portions associated with tubular segments of the bone anchor may be orientated with respect to each other such that in the second configuration, a continuous bone thread is provided along an outer surface of the bone anchor. The orientation is not changed when the bone anchor assumes the first configuration, allowing for adjustments of the position of the bone anchor after implantation by reverting to the second configuration.

The dynamic bone anchor may comprise a head that can assume various designs. In particular, a spherical head can be used, rendering the dynamic bone anchor suitable in combination with receiving parts of polyaxial bone screws or with bone plates comprising holes with spherical seats for pivotably accommodating the bone screws.

BRIEF DESCRIPTION OF THE DRAWINGS

Further features and advantages of the invention will become apparent from the description of embodiments by means of the accompanying drawings. In the drawings:

FIG. 1 shows a perspective exploded view of a dynamic bone anchor according to a first embodiment.

FIG. 2 shows a perspective view of the bone anchor according to FIG. 1 in an assembled state.

FIG. 3 shows a side view of a core member of the dynamic bone anchor according to FIG. 1.

FIG. 4 shows a bottom side view of a first end of the core member according to FIG. 3.

FIG. 5 shows a perspective view of a tip member of the dynamic bone anchor according to the first embodiment.

FIG. 6 shows a cross-sectional view of the tip member shown in FIG. 5, the cross-section taken in a plane containing a longitudinal axis of the core member.

FIG. 7 shows a perspective view from a bottom of a head of the dynamic bone anchor according to FIG. 1.

FIG. 8 shows a cross-sectional view of the head of FIG. 7, the cross-section taken in a plane containing a longitudinal axis of the core member.

FIG. 12 shows a cross-sectional view of the dynamic bone anchor of FIGS. 1 and 2 in a second configuration, wherein the cross-section is taken in a plane containing the longitudinal axis.

FIG. 13a shows a cross-sectional view of the dynamic bone anchor according to the first embodiment in a first configuration in which the tubular segments are spaced apart from each other by a small distance.

FIG. 13b shows an enlarged view of a detail of FIG. 13a.

FIG. 23 shows a cross-sectional view of the dynamic bone anchor according to the third embodiment in a second configuration, wherein the section is taken in a plane containing a longitudinal axis of the bone anchor.

FIG. 24a shows a cross-sectional view of the dynamic bone anchor of FIG. 23 in a first configuration in which the tubular segments are spaced apart by a small distance.

FIG. 24b shows an enlarged view of a detail of FIG. 24a.

FIG. 28a shows a cross-sectional view of the dynamic bone anchor according to the fourth embodiment in a first configuration wherein the tubular segments are spaced apart from each other by a small distance, the section taken in a plane containing a longitudinal axis of the bone anchor.

FIG. 28b shows an enlarged view of a detail of FIG. 28a.

DETAILED DESCRIPTION

Figure 9:
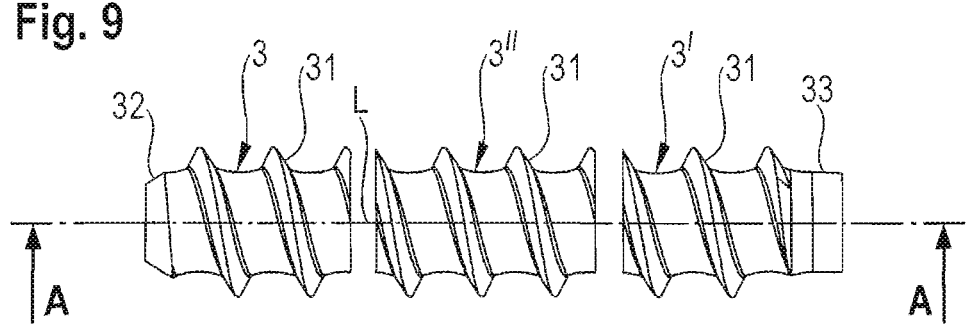
FIG. 9 shows a side view of tubular segments of the dynamic bone anchor in a first configuration according to the first embodiment as shown in FIG. 1.
Figure 10:
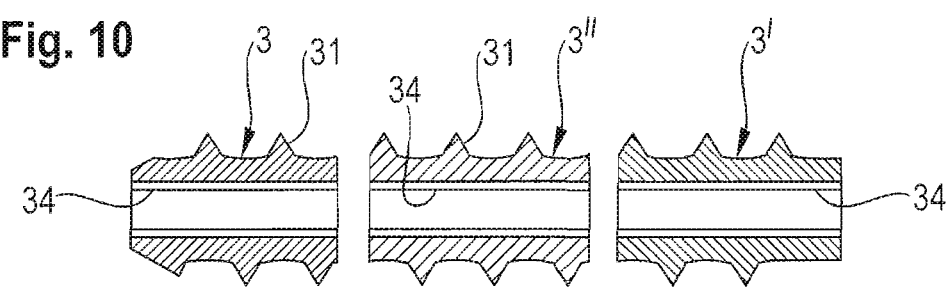
FIG. 10 shows a cross-sectional view of the dynamic bone anchor taken along line A-A in FIG. 9.
Figure 11:
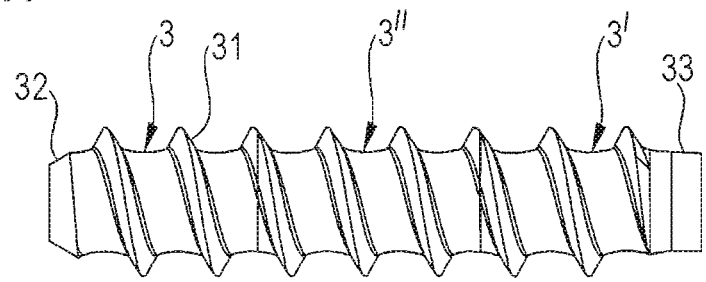
FIG. 11 shows a side view of the tubular segments of FIG. 9 in a second configuration in which the tubular segments abut against each other.

Referring to FIGS. 1 and 2, a dynamic bone anchor 1 according to a first embodiment includes a core member 2, a plurality of tubular segments 3, 3', 3", a tip member 4, and a head 5. The tubular segments 3, 3', 3" can be placed onto the core member 2, and the tip member 4 and the head 5 can be connected to the core member 2 to form the bone anchor 1. Referring further to FIG. 3, the core member 2 comprises a first end 21, an opposite second end 22, and a longitudinal axis L extending through the first end 21 and the second end 22 and forming a central axis of the bone anchor when the core member 2 is not bent or deflected.

The core member 2 can have a tip at the first end 21, and a connection structure 23 adjacent to the tip 21, which can be threaded, as shown in FIG. 3. A central portion 24 between the connection structure 23 and the second end 22 is rod-shaped, having a circular cross-section. At a distance from the connection structure 23, a plurality of connection portions 25 are provided along a length of the central portion 24, wherein the connection portions 25 are spaced apart from each other equidistantly. The connection portions 25 have a square-shaped outer contour, as can be seen in FIGS. 1 and 4, and a thickness such that they extend beyond an outer surface of the rod-shaped portion 24 in a radial direction. In the embodiment shown, three connection portions 25 are provided that serve for connecting the three tubular segments 3, 3', 3", shown in FIG. 1, to the core member 2. At a distance from the last connection portion 25 toward the second end 22, a further connection portion 26 is provided that serves for connecting the head 5 to the core member 2, as explained below. The connection portion 26 also has a square-shaped outer contour. Adjacent to the connection portion 26 in a direction towards the second end 22, a cylindrical portion 27 is provided that has an external diameter greater than a diameter of the rod-shaped portion 24, and that is configured to be accommodated in the head 5. Between the cylindrical portion 27 and the second end 22, a predetermined break-off section 28 is provided. The predetermined break-off section 28 is defined by a region of the rod-shaped portion 24 with a reduced outer diameter. The predetermined break-off section 28 serves for adjusting the length of the rod-shaped portion 24 after implantation of the bone anchor 1 into a bone, for example.

The tip member 4 is shaped as a segment of a cone, with a threaded axial hole 41 configured to cooperate with the connection structure 23 as shown in FIGS. 1, 5, and 6. The tip member 4 and a tip portion at the first end 21 of the core member 2 form a tip of the bone anchor 1. When the tip member 4 is screwed onto the core member 2, it abuts against the rod-shaped portion 24 and extends beyond the rod shaped portion 24 in a radial direction, as can be seen, in particular, in FIG. 12. Thereby, a first annular stop surface 42 may be provided for the tubular segments 3, 3', 3".

The head 5 will be explained with reference to FIGS. 7 and 8. The head 5 comprises a first end 51, an opposite second end 52, and a spherical segment-shaped portion 53 adjacent to the first end 51. Between the spherical-segment shaped portion 53 and the second end 52, a short neck portion 54 is present that has a substantially cylindrical shape. A second recess 55 with a square-shaped inner contour extends from the second end 52 into the spherical-segment portion 53. The second recess 55 serves for accommodating the connection portion 26 of the core member 2, and is adapted to provide a form-fit connection between the connection portion 26 and the head 5.

A tubular shaft of the bone anchor 1 is divided into a plurality of tubular segments 3, 3', 3", wherein a first end tubular segment 3 is adjacent to the tip member 4, a second end tubular segment 3' is adjacent to the head 5, and one or more intermediate tubular segments 3" are provided therebetween. Each of the tubular segments 3, 3', 3" comprises a bone thread 31 at its outer surface. When the tubular segments 3, 3', 3" abut against each other, the bone thread 31 on each tubular member 3, 3', 3" fits to align with the bone thread of the abutting tubular segment 3, 3', 3", so that a continuous tubular shaft with a continuous bone thread 31 is formed. The first end tubular segment 3 may have a tapering portion 32 that tapers towards the first end 21 of the core member 2 when the tubular segments 3, 3', 3" are placed onto the core member 2. The second end tubular segment 3' may comprise a cylindrical portion 33 that is directed towards the second end 22 of the core member 2. The cylindrical portion 33 and the tapering portion 32 are not threaded. It should be understood that the bone thread 31 can be any suitable bone thread. It is not necessary that the bone thread 31 extends fully over each tubular segment 3, 3', 3", nor is it necessary that the bone thread 31 is present on all tubular segments 3, 3', 3".

The inside 34 of each of the tubular segments 3, 3', 3" is hollow, and may have a contour in a plane perpendicular to the longitudinal axis L that is adapted to the shape of the connection portions 25 of the core member 2. In the embodiment shown, the inside 34 is square-shaped. However, corresponding to the shape of the connection portions 25, any polygonal or otherwise formed shape is possible that prevents rotation of the tubular segments 3, 3', 3" around the longitudinal axis L when the tubular segments 3, 3', 3" are placed onto the connection portions 25.

A length of the tubular segments 3, 3', 3" is such that when the tubular segments 3, 3', 3" are placed onto the core member 2 and abut against the tip member 4, there is a distance between the connection portion 26 and a free end of the second end tubular segment 3'.

The materials of the core member 2, the tubular segments 3, 3', 3", the tip member 4, and the head 5, in an example embodiment, are body-compatible, such as a body-compatible metal, for example titanium or stainless steel, a body-compatible metal alloy, for example a nickel titanium alloy such as Nitinol, or a body-compatible polymer material, for example polyetheretherketone (PEEK). The parts can all be made of the same or of different materials.

The dynamic bone anchor 1 is assembled as follows. The core member 2 is guided through first and second recesses 56, 55 of the head 5 with the first end 21, until the cylindrical portion 27 is accommodated in the first recess 56 of the head 5 and abuts against a bottom abutment 56a of the first recess 56. Then, the tubular segments 3, 3', 3" are placed onto the core member 2 such that each tubular segment 3, 3', 3" is positioned on a connection portion 25. Thereafter, the tip member 4 is mounted onto the core member 2. A portion of the core member 2 adjacent to the second end 22 acts as a traction or gripping portion.

In the assembled state, the dynamic bone anchor 1 can assume a first configuration in which the tubular segments 3, 3', 3" are rotationally fixed on the core member 2 but are slidable in an axial direction in a limited manner because there is a small distance between them. In the first configuration, because the tubular segments 3, 3', 3" can move to a limited extent in the axial direction, the core member 2 with the head 5 is able to move relative to the tubular segments 3, 3', 3" in a direction away from the longitudinal axis L.

The dynamic bone anchor 1 can assume a second configuration, in which the second end 52 of the head 5 abuts against a free end of the second end tubular segment 3' and shifts the tubular segments 3, 3', 3" towards the first annular stop surface 42 at the tip member 4. In the second configuration, the tubular segments 3, 3', 3" are not movable in an axial direction. As in the first configuration, the tubular segments 3, 3', 3" are also not rotatable.

In use, the core member 2 is engaged by a tool (not shown) and drawn away from the first end 51 of the head 5, while the head 5 may serve as an abutment for the tool. In this embodiment, the head 5 presses onto the second end tubular segment 3', as shown in FIG. 12, and shifts all the tubular segments 3, 3', 3" towards the tip member 4. The distance between the tubular segments 3, 3', 3" is eliminated, and the whole bone anchor 1 has a continuous bone thread 31 on its outer surface. In this second configuration, the head 5 and the tubular segments 3, 3', 3" are pre-tensioned. The bone anchor 1 is rigid, or in other words, there is no relative movement of the parts. The bone anchor 1 can then be inserted into a bone part or a vertebra, for example. The insertion force is transmitted via the connection portions 25 onto the tubular segments 3, 3', 3". Because the tubular segments 3, 3', 3" cannot rotate, the orientation of the threads 31 with respect to each other is maintained.

After insertion of the bone anchor 1 into a bone part or vertebra, the core member 2 is released by the tool so that the pre-tension is not maintained. The head 5 can move slightly in an axial direction so that the cylindrical portion 27 abuts against the abutment 56a in the head 5. As a result, small gaps emerge between the tubular segments 3, 3', 3" that allow a limited motion of the tubular segments 3, 3', 3" relative to each other. As shown in FIG. 13a, the head 5 with the core member 2 can perform a small translational and/or rotational movement with respect to the tubular segments 3, 3', 3" in a direction transverse to the longitudinal axis L. Such a movement is based on a deflection of the core member 2 away from a straight position, which is possible due to a gap 26a between the rod-shaped portion 24 of the core member 2 and the tubular segments 3, 3', 3" (FIG. 13b). As can be further seen in FIG. 13b, because the tubular segments 3, 3', 3" are movable to a limited extent, the second end 52 of the head 5 is movable with respect to the second end tubular segment 3'.

Finally, the core member 2 can be shortened by breaking-off the second end 22 at the predetermined break-off section 28.

Figure 14:
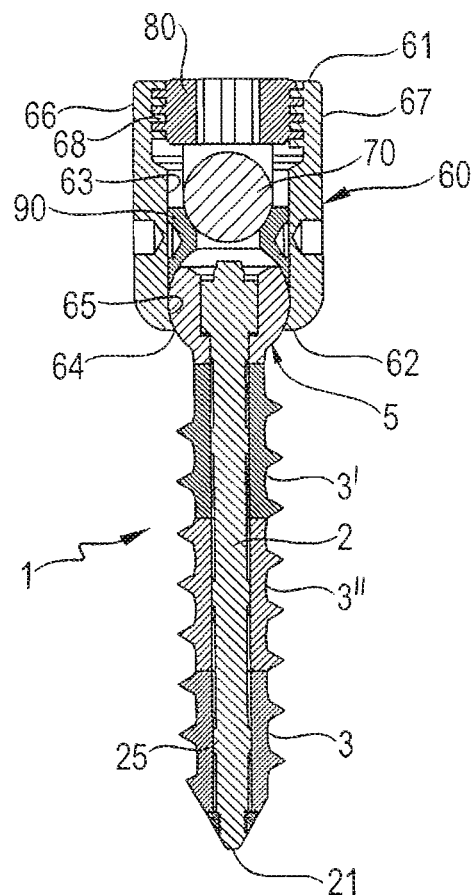
FIG. 14 shows a cross-sectional view of a polyaxial pedicle screw with the dynamic bone anchor according to the first embodiment used as an anchoring element.

A first application of the bone anchor 1 together with a stabilization device is shown in FIG. 14. The bone anchor 1 according to the first embodiment is coupled to a receiving part 60 to form a polyaxial bone anchor. The receiving part 60 is substantially cylindrical and comprises a top end 61, a bottom end 62, and a coaxial bore 63 extending from the top end 61 to a distance from the bottom end 62. The bore 63 narrows towards the bottom end 62 and provides an opening 64 near the bottom end 62. Near the opening 64, a seat 65 is provided for pivotably receiving the head 5. A U-shaped recess extends from the top end 61 to a distance from the top end 61 for receiving a stabilization rod 70. By means of the U-shaped recess two free legs 66, 67 are provided, which have an internal thread 68 for cooperating with a locking member such as a set screw 80. Furthermore, a pressure member 90 is provided that exerts pressure onto the head 5, such that the head 5 can be locked in a certain angular position by tightening the locking member 80. The bone anchor 1 may be used with other designs of receiving parts 80 and polyaxial bone screws. Also the head 5 of the core member 2 may be designed such that it comprises a section for receiving a rod and for receiving a locking member to fix the rod as known from other monoaxial bone screws.

In use, at least two polyaxial bone anchors are inserted into adjacent vertebrae or bone parts and connected via the rod 70. Once the bone anchors 1 are inserted into the bone parts or adjacent vertebrae, the heads 5 can perform a limited motion with respect to the tubular segments 3, 3', 3". Once a head 5 is locked in the receiving part 60, the bone anchor 1 provides for a dynamic stabilization that allows small movements of the bone parts with respect to each other or small movements of a motion segment of the spinal column.

Figure 15:
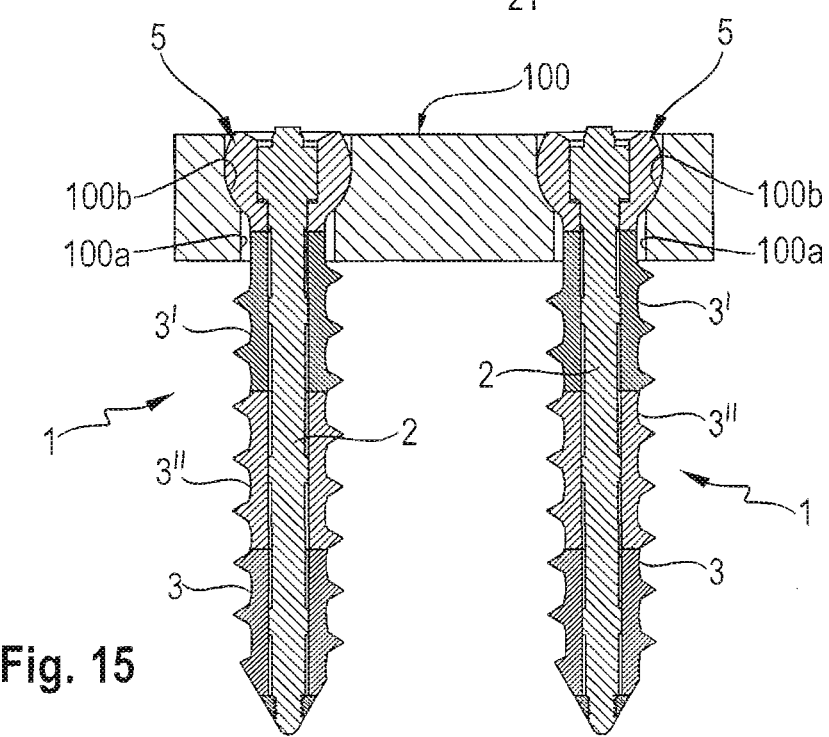
FIG. 15 shows a cross-sectional view of the dynamic bone anchor according to the first embodiment used with a bone plate.
Figure 16:
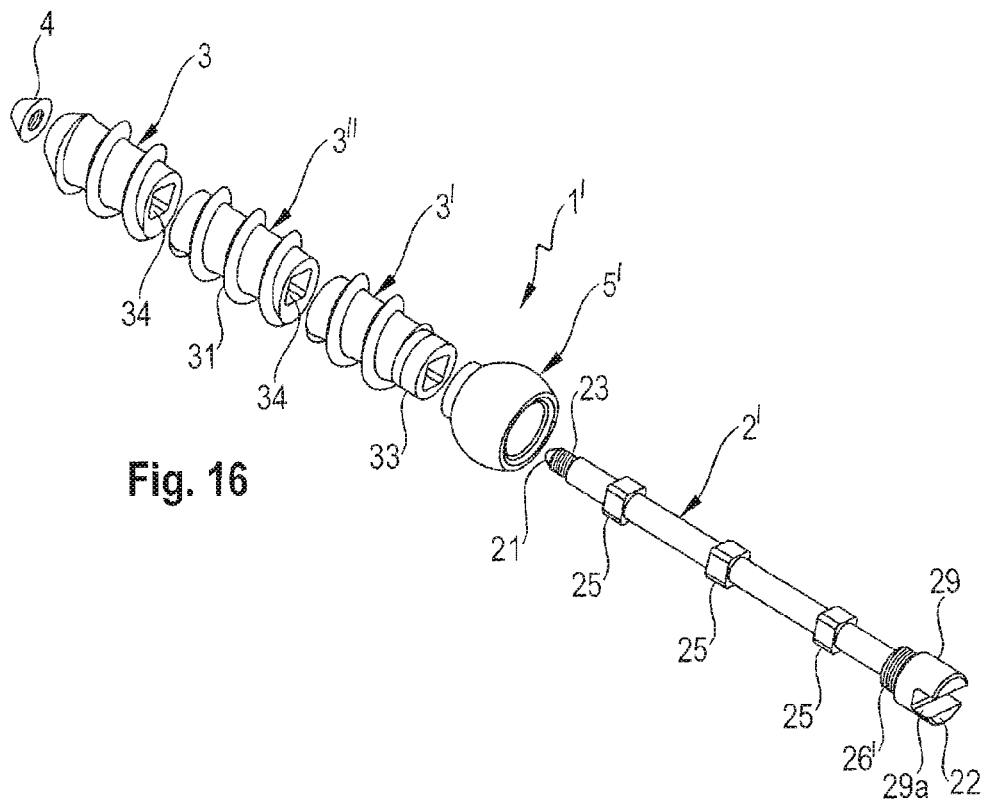
FIG. 16 shows a perspective exploded view of a dynamic bone anchor according to a second embodiment.

A second example of an application is shown in FIG. 15, wherein bone anchors 1 according to the first embodiment are used together with a bone plate 100 comprising holes 100a with seat portions 100b for receiving the heads 5 of the two bone anchors 1, respectively. The two bone anchors 1 are inserted in adjacent bone parts with the bone plate 100 bridging at least a portion of a bone fracture site. In a specific application, a distance between a center axis of the two holes 100a is slightly smaller than a distance between the longitudinal axis L of the bone anchors 1. Because the heads 5 with the core members 2 can move slightly in a direction transverse to the longitudinal axis L, the bone parts can be drawn together at the fracture site.

A second embodiment of the dynamic bone anchor 1' will be explained with reference to FIGS. 16 to 19. The dynamic bone anchor 1' of the second embodiment differs from the dynamic bone anchor 1 of the first embodiment in the design of the core member 2' and the head 5'. Parts that are identical or similar to the first embodiment are indicated with the same reference numerals, and the descriptions thereof will not be repeated. The core member 2' comprises, adjacent to its second end 22, a cylindrical portion 29 with an engagement portion configured to receive a tool, for example a slot 29a.

Following the cylindrical portion 29, there is a threaded connection portion 26' with an outer thread that is configured to cooperate with a corresponding thread provided in the head 5'. The head 5' shown in FIGS. 18 and 19, differs from the head 5 in that the second recess 55' that serves for connection to the core member 2' is circular and has an internal thread that cooperates with the threaded connection portion 26' of the core member 2'.

Figure 17:
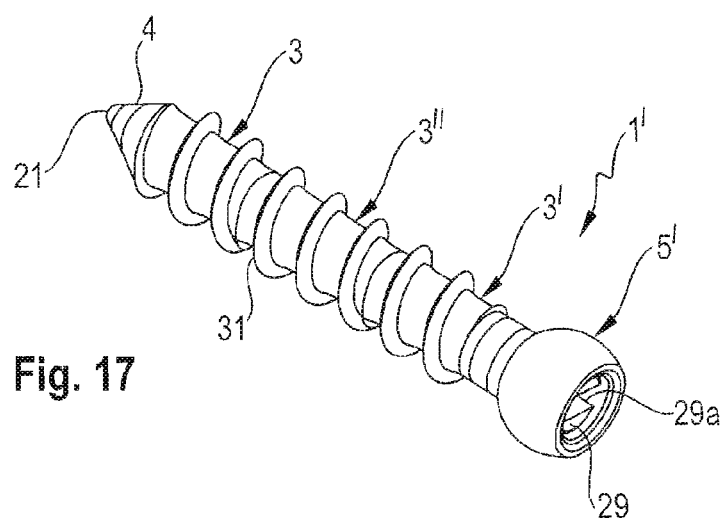
FIG. 17 shows a perspective view of the dynamic bone anchor according to the second embodiment of FIG. 16 in an assembled state.
Figure 18:
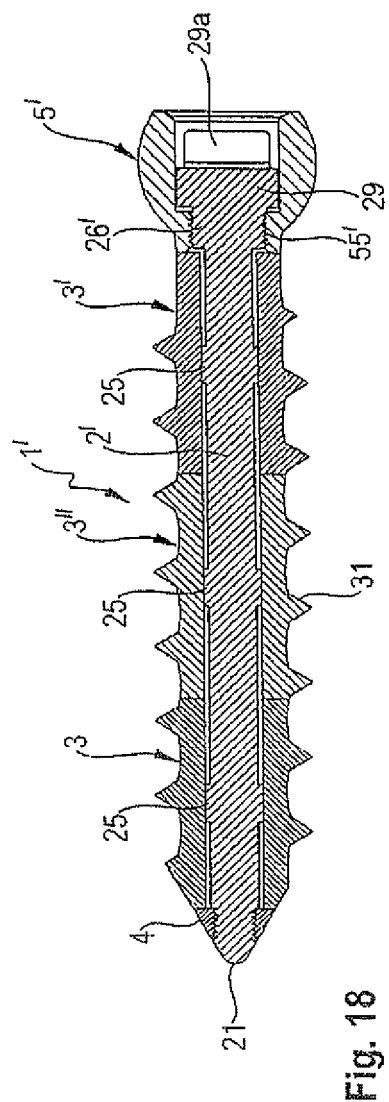
FIG. 18 shows a cross-sectional view of the dynamic bone anchor according to the second embodiment in a second configuration, the cross-section taken in a plane containing a longitudinal axis of the bone anchor.
Figure 19:
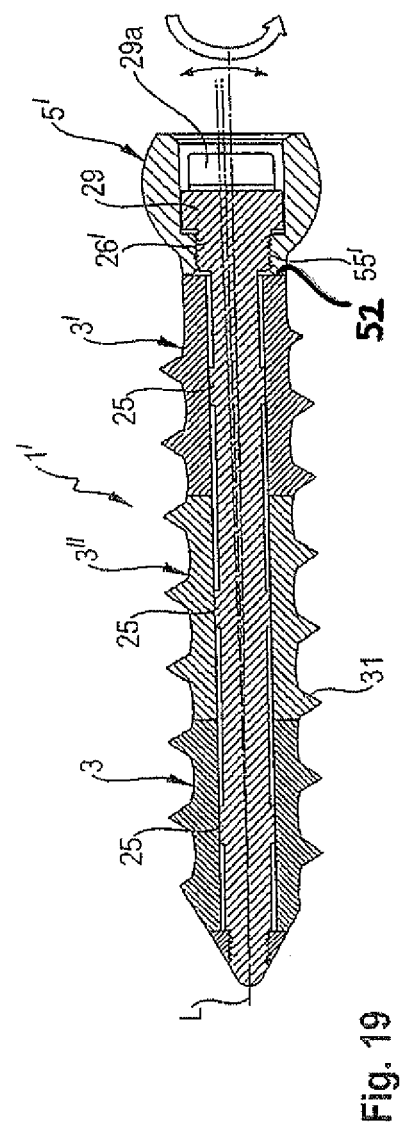
FIG. 19 shows a cross-sectional view of the dynamic bone anchor of FIG. 18 in a first configuration in which the tubular segments are spaced apart from each other by a small distance.
Figure 20:
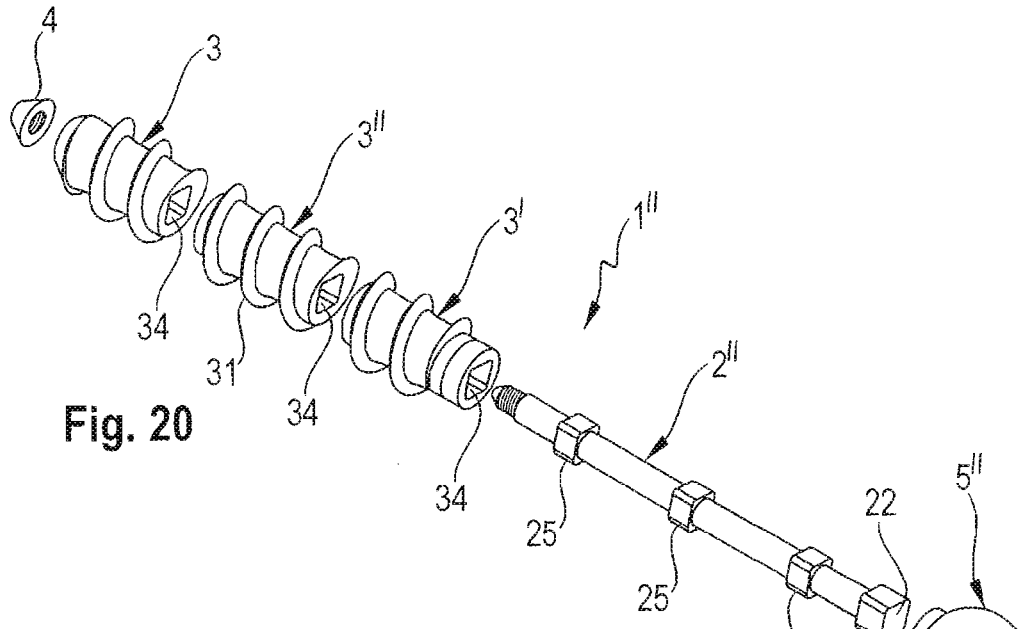
FIG. 20 shows a perspective exploded view of a dynamic bone anchor according to a third embodiment.
Figure 21:
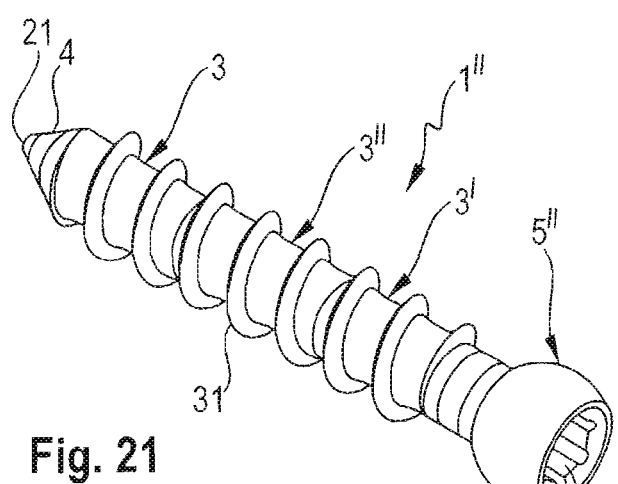
FIG. 21 shows a perspective view of the dynamic bone anchor of FIG. 20 in an assembled state.
Figure 22:
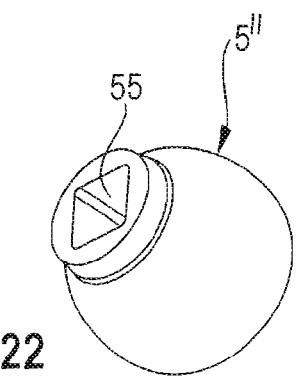
FIG. 22 shows a perspective view from the bottom onto a head of the dynamic bone anchor according to the third embodiment.
Figure 25:
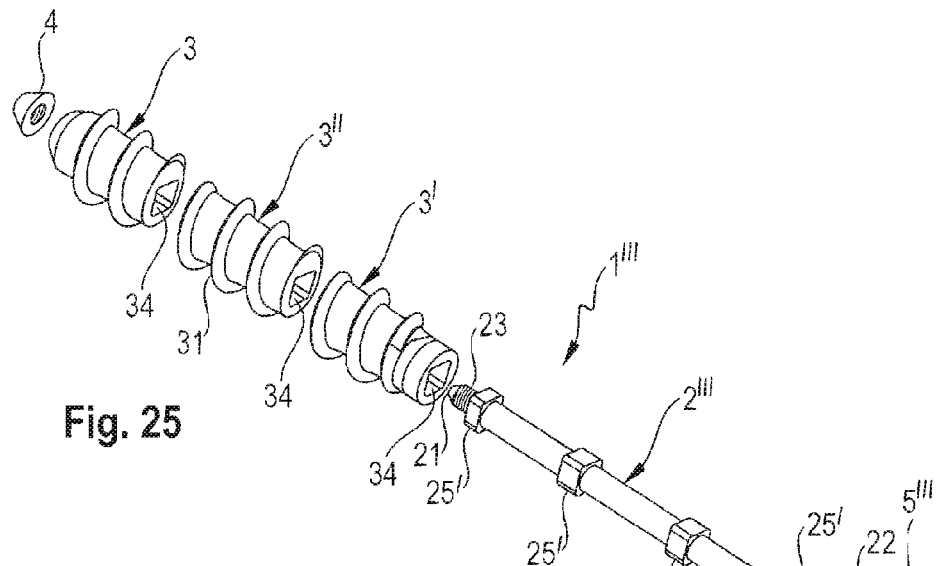
FIG. 25 shows a perspective exploded view of a dynamic bone anchor according to a fourth embodiment.
Figure 26:
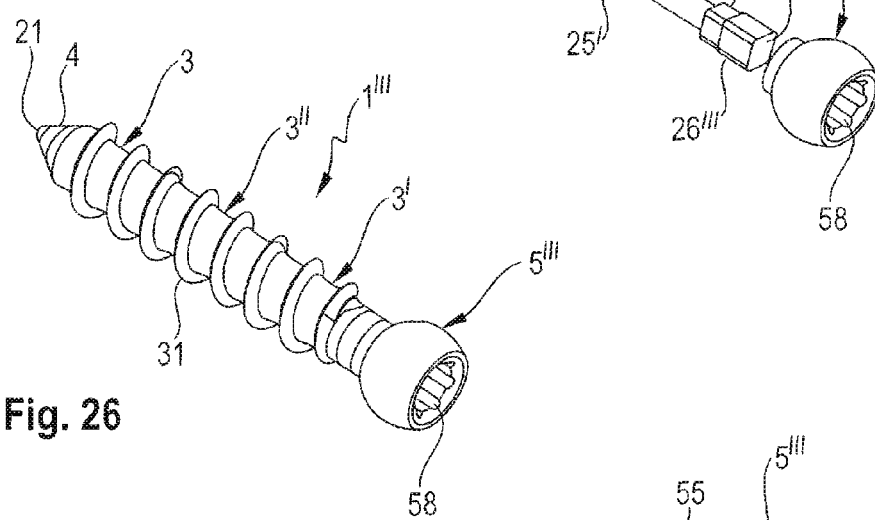
FIG. 26 shows a perspective view of the dynamic bone anchor according to FIG. 25 in an assembled state.
Figure 27:
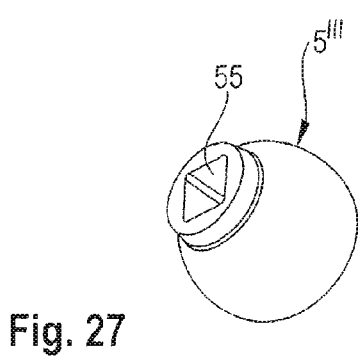
FIG. 27 shows a perspective view from the bottom onto a head of the dynamic bone anchor according to the fourth embodiment.

In the assembled state shown in FIGS. 17 to 19, the head 5' is screwed onto the core member 2' and presses with a free second end 52 onto a free end surface of the second end tubular section 3'. By means of the threaded connection between the core member 2' and the head 5', the tubular segments 3, 3', 3" can be pre-tensioned with respect to the core member 2' by pressing the tubular segments 3, 3', 3" against the tip member 4. In this second configuration shown in FIG. 18, the dynamic bone anchor 1' is rigid. The dynamic bone anchor 1' can be inserted into a bone in the second configuration. For example, the slot 29a can be engaged with a tool and the whole bone anchor 1' can be screwed into the bone.

After insertion into the bone, the core member 2' can be screwed backward relative to the head 5' until the cylindrical portion 29 abuts against the abutment 56a in the first recess 56 (as shown in FIG. 19), depicting the first configuration of the bone anchor 1'. Thereby, the pre-tension is released and the tubular segments 3, 3', 3" are movable in an axial direction to a limited extent.

A third embodiment of the dynamic bone anchor 1" will be described with reference to FIGS. 20 to 24b. The third embodiment of the bone anchor 1" differs from the previous embodiments by the design of the core member 2" and the head 5". All other parts are similar or identical to the previous embodiments, and the descriptions thereof will not be repeated. The core member 2" comprises a connection portion 26" for connection to the head 5". The connection portion 26" has an outer polygonal contour, in particular a square-shaped contour, that is configured to be connected to the corresponding square-shaped second recess 55 of the head 5" by a press-fit connection. At an opposite side, the head 5" has an engagement portion for a tool, for example, a torx-shaped recess 58.

The core member 2" is made of a material that is based on a nickel-titanium based shape memory alloy, preferably Nitinol. The material exhibits shape memory properties.

The core member 2" is connected to the head 5" via a press-fit connection achieved through the shape memory effect of the material. For example, the connection portion 26" is cooled below the martensite finish temperature ($M_f$) so that the flat sides of the connection portion 26" are impressed. Due to the ability of the martensite phase to deform, the connection portion 26" can be easily inserted into the second recess 55, and after heating, can return to the square-shaped contour to achieve the press-fit connection.

The shape memory effect of the material is also used to provide the first and the second configuration of the bone anchor 1". First, the core 2" can be cooled below the martensite finish temperature ($M_f$) before mounting, and can be slightly compressed in a longitudinal direction, whereby its length is shortened. In the martensite metallurgical state, the core member 2" and head 5" are assembled with the tubular segments 3, 3', 3" and the tip member 4. After heating above an austenite finish temperature ($A_f$), the core member 2" assumes its original non-compressed state and its original length. The elongation of the core member 2" after heating moves the head 5" away from the tubular segments 3, 3', 3" so that the tubular segments 3, 3', 3" become movable with respect to each other in an axial direction.

The heating can be carried out by the application of body temperature, for example, when the bone anchor 1" is inserted into a bone, or can be carried out through a separate heating step with an external heating device.

A fourth embodiment of the dynamic bone anchor 1' will be described with reference to FIGS. 25 to 28b. The fourth embodiment of the dynamic bone anchor 1''' differs from the previous embodiments in the design of the core member 2''' and the head 5'''. Parts that are similar or identical to those of the previous embodiments have the same reference numerals, and the descriptions thereof will not be repeated. The core member 2''' comprises, adjacent to the threaded connection structure 23, a first connection portion 25' that has a square-shaped outer contour, as do the other connection portions 25', and provides for a greater abutment surface for the tip member 4. The other connection portions 25' are provided at positions P1, P2, etc. corresponding to positions at which ends of the tubular segments 3, 3', 3" abut against each other, as shown in detail in FIG. 28a. Hence, the tubular segments 3, 3', 3" are supported by the connection portions 25' at their respective free ends. Adjacent to its second end 22, the core member 2''' comprises a connection portion 26''' with a square-shaped outer contour, similar to the third embodiment. The head 5''' is similar to the head 5" of the third embodiment and has a square-shaped second recess 55 for connection with the connection portion 26''', and opposite to an engagement portion 58 for engagement with a tool. The connection portion 26''' extends in a radial direction beyond the connection portions 25'. Furthermore an axial length of the connection portion 26''' may be slightly shorter than a depth of the second recess 55 in the head 5''', so that a small gap 27a may be provided within a neck portion of the head 5''' that further facilitates movement of the head 5''' in the first configuration. The connection portion 26''' can be connected to the head 5''', for example, by a press-fit connection.

As in the previous embodiments, a configuration, shown in FIGS. 28a and 28b, is provided in which the tubular segments 3, 3', 3" are movable with respect to each other, and wherein the head 5''' can perform a limited motion with respect to the tubular segments 3, 3', 3". Meanwhile, the dynamic bone anchor 1''' can be inserted into a bone in a compressed configuration, similarly as discussed with respect to previous embodiments, because higher forces can be transmitted via abutting end surfaces of the tubular segments 3, 3', 3".

It should be understood that for the fourth embodiment, the core member 2''' can be made of a Nickel-Titanium (NiTi) shape memory alloy, such as Nitinol. Also in this embodiment, the core member 2''' may be shortened by compressing it during its martensite phase, and can be elongated by heating after insertion of the bone anchor 1' into a bone. Therefore, it is possible to obtain two dynamic configurations of the dynamic bone anchor 1''' with different sizes of gaps.

Further adaptations or modifications of the dynamic bone anchor described in the embodiments can be accomplished by one of ordinary skill in the art without departing from the scope of the invention. For example, the head may have any other shape suitable for connecting it to other stabilization devices such as bone plates, receiving parts for accommodating stabilization rods, etc. The head may even be omitted in some embodiments, if a free end of the core member is suitable for connection to another device.

Any kinds of tips may be provided at the first end 21. The tip member 4, for example, can be a full cone, and the first end 21 can be only provided with a connection structure to connect to the tip member 4.

For the bone engagement structure, barbs or any other bone engagement structures, for example, a roughened surface, may be provided.

At least one tubular segment, and preferably two or more tubular segments may be provided.

The features of different embodiments may also be combined with each other.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A dynamic bone anchor comprising:
a longitudinal core member having a first end and a second end, a longitudinal axis extending through the first end and the second end, and at least one connection portion having a larger cross section than a cross section of a second portion of the core member;
a plurality of tubular segments configured to be positioned around the core member, each of the tubular segments having a bone engagement structure on an outer surface thereof;
wherein in a first assembled configuration, each of the tubular segments is movable on the core member along the longitudinal axis and the at least one connection portion of the core member prevents rotation of the plurality of tubular segments relative to the core member.

2. The dynamic bone anchor of claim 1, wherein in the first assembled configuration the core member is configured to be movable relative to the tubular segments in a direction transverse to the longitudinal axis.

3. The dynamic bone anchor of claim 1, wherein in the first assembled configuration, each of the tubular segments is configured to slide along the core member and is fixed against rotation around the longitudinal axis.

4. The dynamic bone anchor of claim 1, wherein an inner surface of each of the tubular segments comprises a contour having a non-circular shape in a plane perpendicular to the longitudinal axis, and wherein the at least one connection portion is configured to couple to at least one of the tubular segments with a corresponding outer contour of the core member.

5. The dynamic bone anchor of claim 4, wherein the contour of the tubular segments is square-shaped.

6. The dynamic bone anchor of claim 1, wherein an outer surface of each of the tubular segments comprises a bone thread.

7. The dynamic bone anchor of claim 6, wherein in a second assembled configuration where the tubular segments are not moveable on the core member, a continuous bone thread is provided along the outer surface of the tubular segments.

8. The dynamic bone anchor of claim 7, wherein the bone anchor is configured to move from the first assembled configuration into the second assembled configuration.

9. The dynamic bone anchor of claim 7, wherein the bone anchor is configured to move from the second assembled configuration into the first assembled configuration.

10. The dynamic bone anchor of claim 1, wherein in the first assembled configuration, a first stop and a second stop on the core member are configured to limit the motion of the tubular segments along the longitudinal axis.

11. The dynamic bone anchor of claim 10, wherein the first stop comprises a tip member at or near the first end of the core member, the tip member being a connectable tip member.

12. The dynamic bone anchor of claim 10, further comprising a head at or near a second end of the core member, the head comprising the second stop.

13. The dynamic bone anchor of claim 12, wherein the head is configured to slide along the core member such that the head can move against the tubular segments.

14. The dynamic bone anchor of claim 13, wherein the core member comprises a traction portion at its second end, and wherein the bone anchor is configured to be brought into a second assembled configuration by pulling the core member and traction portion and pressing the head against the tubular segments such that the tubular segments are fixed with respect to the core member.

15. The dynamic bone anchor of claim 14, wherein the core member comprises a predetermined break-off section located a distance from its second end.

16. The dynamic bone anchor of claim 14, wherein the head is configured to connect to the core member at an adjustable distance from the tubular segments along a longitudinal direction, and wherein the connection is by a threaded connection.

17. The dynamic bone anchor of claim 14, wherein in the second assembled configuration, the tubular segments are fixed with respect to the core member.

18. The dynamic bone anchor of claim 1, wherein the core member comprises a material having shape memory properties, wherein the core member is configured to assume a first length in the first assembled configuration and a second length in a second assembled configuration, and wherein the first length is greater than the second length.

19. The dynamic bone anchor of claim 18, wherein the core member is configured to change from the second length to the first length upon an application of heat treatment.

20. The dynamic bone anchor of claim 1, wherein the plurality of tubular segments comprises at least two tubular segments, and wherein a single connection portion is configured to bridge respective adjacent ends of two tubular segments.

21. The dynamic bone anchor of claim 1, further comprising a head at the second end of the core member, wherein in the first assembled configuration, the head is moveable relative to the tubular segments in a direction transverse to the longitudinal axis.

* * * * *